(12) United States Patent
Miura et al.

(10) Patent No.: US 6,642,419 B1
(45) Date of Patent: Nov. 4, 2003

(54) OXIDATION METHOD

(75) Inventors: Hiroyuki Miura, Takasago (JP); Hitoshi Watanabe, Himeji (JP); Tomohide Ina, Himeji (JP); Hidehiko Nakajima, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/673,564

(22) PCT Filed: Feb. 8, 2000

(86) PCT No.: PCT/JP00/00689

§ 371 (c)(1),
(2), (4) Date: Oct. 18, 2000

(87) PCT Pub. No.: WO00/48972

PCT Pub. Date: Aug. 24, 2000

(30) Foreign Application Priority Data

Feb. 19, 1999 (JP) ............................................ 11-042104

(51) Int. Cl.[7] ........................ C07C 45/00; C07C 47/00; C07C 35/08; C07C 51/16
(52) U.S. Cl. ....................... 568/357; 568/431; 568/836; 562/549; 562/409
(58) Field of Search ................. 568/357, 431, 568/836; 562/549, 409

(56) References Cited

U.S. PATENT DOCUMENTS 5,958,821 A * 9/1999 Ishii et al. .................. 502/167

FOREIGN PATENT DOCUMENTS

| EP | A1824962 | 2/1998 |
|---|---|---|
| JP | A838909 | 2/1996 |
| JP | A987215 | 3/1997 |
| JP | A9143109 | 6/1997 |
| JP | A9278675 | 10/1997 |
| JP | A9327626 | 12/1997 |
| JP | A1057814 | 3/1998 |

* cited by examiner

Primary Examiner—J. Parsa
(74) Attorney, Agent, or Firm—Birch, Stewart, Kolasch & Birch, LLP

(57) ABSTRACT

In the presence of (1) an oxidizing catalyst comprising an imide compound such as N-hydroxyphthalimide, or (2) an oxidizing catalyst comprising such imide compound and a transition metal element-containing compound as a co-oxidizing agent (e. g., oxides, halides, complexes, hetero polyacid salts) a hydrocaron, an alcohol, an aldehyde, or a ketone as a substrate is brought into contact with molecular oxygen for oxidation. In the above-described oxidation process, the water content of the oxidizing reaction system is 200 mol or lower relative to 1 mol of the imide compound. According to the present invention, a substrate is efficiently oxidized with molecular oxygen under mild conditions, and there can be obtained the object compound(s) of high quality.

12 Claims, No Drawings

OXIDATION METHOD

This application is the national phase under 35 U.S.C. §371 of PCT International Application No. PCT/JP00/00689 which has an International filing date of Feb. 8, 2000, which designated the United States of America.

TECHNICAL FIELD

The present invention relates to an oxidation process which employs an oxidizing catalyst useful for producing alcohols, carbonyl compounds, organic acids, or the like.

BACKGROUND TECHNOLOGY

Imide compounds such as N-hydroxyphthalimide are known as catalysts used when oxidizing a substrate such as a hydrocarbon, an alcohol, an aldehyde, a ketone, an amine, or a heterocyclic compound by bringing the substrate into contact with molecular oxygen [Japanese Patent Application Laid-Open No. 38909/1996 (JP-A-8-38909), Japanese Patent Application Laid-Open No. 278675/1997 (JP-A-9-278675), Japanese Patent Application Laid-Open No. 327626/1997 (JP-A-9-327626), Japanese Patent Application Laid-Open No. 57814/1998 (JP-A-10-57814)]. An oxidation reaction which employs such catalyst does not particularly require the treatment of exhaust gas, and oxidation products such as alcohols, aldehydes, ketones, and organic acids can be effectively produced under mild conditions at high conversions and selectivities.

However, in a process which employs such catalyst and a co-oxidizing agent, the purity and yield of an object product may sometimes be deteriorated, because by-product(s) difficult to separate from the object compound is generated as a result of deterioration in the activity of the co-oxidizing agent or the oxidizing catalyst (oxidation catalyst). For instance, when cyclohexane, N-hydroxyphthalimide, and cobalt are employed as the substrate, the oxidizing catalyst and the co-oxidizing agent respectively, cyclohexanol, cyclohexanone, and adipic acid are formed. However, when cyclohexanone is produced through a reaction with such reaction system, cobalt as the co-oxidizing agent is poisoned and consequently the catalytic amount of cobalt is substantially reduced. When the catalytic amount of cobalt is small, in the oxidizing reaction step, the formed peroxide is not decomposed sufficiently and therefore a large amount of the peroxide remains in the oxidation reaction mixture. As a result, a product such as the peroxide or an acid derived therefrom by post-treatment is left unseparated in cyclohexanone even after rectification, giving bad influence on the quality of cyclohexanone. Such consequence can be seen not only in the above reaction but also in the case where a catalyst constituted of only the aforementioned imide compound, particularly a catalytic system comprising the imide compound and a co-catalyst is employed in a reaction.

Thus, an object of the present invention is to provide a process which enables the oxidation of a substrate with molecular oxygen without the use of a specific reducing agent while inhibiting the generation of a by-product(s) even when the aforementioned imide compound is employed as an oxidizing catalyst in the reaction.

Another object of the present invention is to provide an oxidation process which makes it possible to smoothly oxidize a substrate while inhibiting the deactivation of an oxidizing catalyst or an oxidizing catalytic system.

Still another object of the present invention is to provide an oxidation process which enables, even under mild conditions, the production of an object compound using molecular oxygen with high purity and in high yield.

A further object of the present invention is to provide an oxidation process which enable the production of, under mild conditions, alcohols, carbonyl compounds, aldehyde compounds, and organic carboxylic acids with high purity and in high yields.

A still further object of the present invention is to provide an oxidation process which enables the production of, under mild conditions, cyclohexanone and cyclohexanol (KA oil), and adipic acid using molecular oxygen with high purity and in high yields.

DISCLOSURE OF THE INVENTION

The inventors of the present invention made intensive and extensive studies to achieve the above objects, and finally found that the water content of the oxidizing reaction system gives a large influence upon the activity of an oxidizing catalyst. The present invention is based on the above findings.

That is, the present invention provide an oxidation process comprising a step of bringing a substrate into contact with molecular oxygen in the presence of a compound having an imide unit (hereinafter, sometimes referred to simply as an imide compound) represented by the following formula (1):

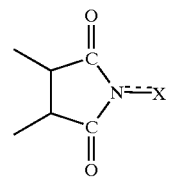

(1)

wherein X stands for an oxygen atom or a hydroxyl group, and the process is characterized in that the water content of thee oxidizing reaction system is not more than 200 mol (for example, about 0 to 50 mol) relative to 1 mol of the imide compound. In the above oxidizing reaction, the imide compound may be a compound represented by the following fomrula (2):

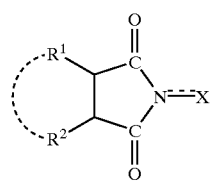

(2)

wherein $R^1$ and $R^2$ are the same or different, each representing a hydrogen atom, a halogen atom, an alkyl group, an aryl group, a cycloalkyl group, a hydroxyl group, an alkoxy group, a carboxyl group, an alkoxycarbonyl group, or an acyl group; $R^1$ and $R^2$ may bond together to form a double bond or an aromatic- or non-aromatic ring; the aromatic- or non-aromatic ring composed of $R^1$ and $R^2$ may have at least one imide unit represented by the aforementioned formula (1); and X has the same meaning as defined above.

$R^1$ and $R^2$ in the formula (2) may be coupled together to form a cyclohexane ring which may have a substituent, a cyclohexene ring which may have a substituent, a 5-norbornene ring which may have a substituent, or a benzene ring which may have a substituent. Moreover, the compound having an imide unit of the formula (1). is employed in combination with a co-oxidizing agent to form an oxidizing catalyst.

In the above oxidation process, the substrate may be at least one member selected from (i) a hydrocarbon having a carbon-hydrogen bond at the allyl site or benzyl site, (ii) a cycloalkane which may have a substituent, (iii) a condensed ring-type hydrocarbon containing a cycloalkane ring or a non-aromatic heterocycle, (iv) a bridged cyclic hydrocarbon containing tertiary carbon, (v) a compound having a hydroxymethyl group at a position adjacent to an unsaturated bond, (vi) an alicyclic alcohol, (vii) an alicyclic alcohol having tertiary carbon, (viii) an aldehyde compound, and (ix) a ketone.

Particularly, the present invention provides an oxidation process useful in producing a cycloalkanone, a cycloalkanol, or a dicarboxylic acid by oxidizing a corresponding cycloalkane which may have a substituent with molecular oxygen.

Moreover, using 0.01 to 0.5 mol of the compound having an imide unit of the formula (1) (if necessary, 0.001 to 0.1 mol of the co-oxidizing agent) relative to 1 mol of a substrate, a water content of the oxidizing reaction system may be maintained of about 0 to 30 mol relative to 1 mol of the compound having an imide unit. Further, a water content of the oxidizing reaction system may be maintained within the above range by removing water produced by the oxidizing reaction from the reaction system. When an oxidizing reaction is conducted in an organic solvent, water resulted from the oxidizing reaction, the solvent and the compound having an imide unit of the formula (1) are separated from the reaction products and the solvent separated is recyclable to the oxidizing reaction system.

BEST MODE FOR CARRYING OUT THE INVENTION

The oxidizing catalyst employed in the oxidation process of the present invention is an imide compound represented by the following formula (1).

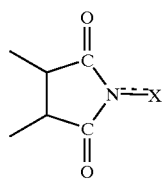

(1)

In the formula (1), X stands for an oxygen atom or a hydroxyl group. A preferred oxidizing catalyst is represented by the following formula (2).

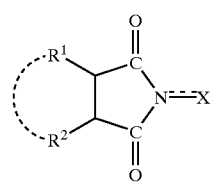

(2)

In a compound of the formula (2), examples of the halogen atom designated by the substituent $R^1$ or $R^2$ include iodine, bromine, chlorine, and fluorine. Alkyl groups include, e.g., straight- or branched-chain alkyl groups having about 1 to 10 carbon atoms such as methyl, ethyl, propyl, isopropyl, butyl, isobutyl, sec-butyl, t-butyl, pentyl, hexyl, heptyl, octyl, and decyl (preferably, $C_{1-6}$ alkyl groups, particularly $C_{1-4}$ alkyl groups).

Aryl groups include phenyl group and naphtyl group, and cycloalkyl groups include $C_{3-10}$ cycloalkyl groups such as cyclopentyl, cyclohexyl, and cyclooctyl groups. Alkoxy groups include alkoxy groups having about 1 to 10 carbon atoms, such as methoxy, ethoxy, propoxy, isopropoxy, butoxy, isobutoxy, t-butoxy, pentyloxy, and hexyloxy, preferably $C_{1-6}$ alkoxy groups, and particularly $C_{1-4}$ alkoxy groups.

Alkoxycarbonyl groups include alkoxycarbonyl groups having about 1 to 10 carbons atoms in an alkoxy moiety (preferably, $C_{1-6}$alkoxy-carbonyl groups, $C_{1-4}$alkoxy-carbonyl groups), such as methoxycarbonyl, ethoxycarbonyl, propoxycarbonyl, isopropoxycarbonyl, butoxycarbonyl, isobutoxycarbonyl, t-butoxycarbonyl, pentyloxycarbonyl, and hexyloxycarbonyl group.

As the acyl group, there may be exemplified those having about 1 to 6 carbon atoms, such as formyl, acetyl, propionyl, butyryl, isobutyryl, valeryl, isovaleryl, and pivaloyl groups.

The substituents $R^1$ and $R^2$ may be the same or different. Moreover, in the formula (2), the substituents $R^1$ and $R^2$ may bond together to form a double bond or an aromatic- or non-aromatic ring. Preferred aromatic- or non-aromatic rings are about 5 to 12-membered ones, particularly about 6 to 10-membered ones. The ring may be a heterocycle or a condensed heterocycle, though a hydrocarbon ring in many cases. The aromatic- or non-aromatic ring may have at least one imide unit represented by the formula (1) (usually, one or two imide units). Examples of such ring include non-aromatic alicyclic rings (e.g., cycloalkane rings which may have a substituent, such as cyclohexane ring; cycloalkene rings which may have a substituent, such as cyclohexene ring); non-aromatic bridged rings (e.g., bridged hydrocarbon rings which may have a substituent, such as 5-norbornene ring); and aromatic rings which may have a substituent, such as benzene ring and naphthalene ring. In many instances, the aforementioned ring is constituted of an aromatic ring.

Included among the preferred imide compounds are compounds expressed by the following formula:

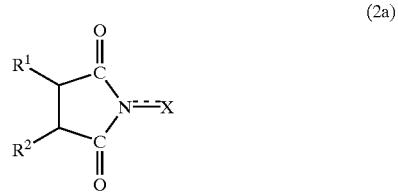

(2a)

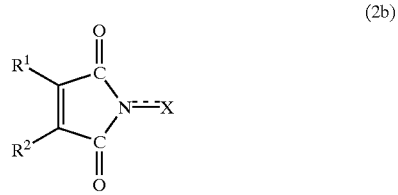

(2b)

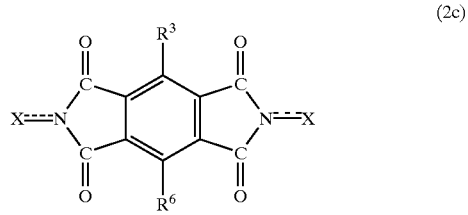

(2c)

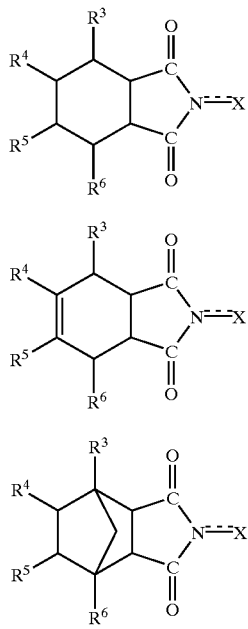

wherein $R^3$ to $R^6$ are the same or different, each representing a hydrogen atom, an alkyl group, a hydroxyl group, an alkoxy group, a carboxyl group, an alkoxycarbonyl group, an acyl group, a nitro group, a cyano group, an amino group, or a halogen atom; and $R^1$, $R^2$, and X have the same meanings as defined above.

As to the substituents $R^3$ to $R^6$, examples of the alkyl group, alkoxyl group, alkoxycarbonyl group, acyl group, and halogen group are similar to those listed above. Usually, the substituents $R^3$ to $R^6$ each stands for, in many instances, a hydrogen atom, a lower alkyl group having about 1 to 4 carbon atoms, a carboxyl group, a nitro group, or a halogen atom.

In the oxidizing reaction, the compounds having an imide group represented by the formula (1) can be used either singly or in combination.

The imide compound of the formula (1) [imide compound (1)] can be prepared by a conventional imidation reaction, for example, by allowing a corresponding acid anhydride to react with hydroxylamine ($NH_2OH$) for ring-opening of an acid anhydride group, and then closing the ring to form an imide.

Examples of a preferred imide compound (1) include N-hydroxysuccinimide, N-hydroxymaleimide, N-hydroxyhexa-hydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxy-pyromellitimide, N,N'-dihydroxynaphthalenetetracarboximide. A particularly preferred compound includes an N-hydroxyimide compound derived from an alicyclic polycarboxylic anhydride, especially one derived from an aromatic polycarboxylic anhydride, such as N-hydroxyphthalimide.

The use of such imide compound makes it possible to improve the oxidation activity without employing a co-oxidizing agent such as copper chloride, and an oxidizing reaction is catalytically facilitated even under mild conditions. Thus, substrates are efficiently oxidizable with high selectivities, and there can be formed alcohols, ketones, aldehydes, and organic carboxylic acids. Moreover, when a substrate is oxidized in the co-presence of an imide compound (1) and a co-oxidizing agent, the conversion and/or selectivity is further improved.

Examples of the co-oxidizing agent as a co-catalyst (promoter) include metal compounds, such as transition metal element-containing compounds and compounds containing a Group 13 element of the Periodic Table of Elements (e.g., boron B, Aluminum Al) typified by a boron compound. The co-oxidizing agent can be used either singly or in combination with other co-oxidizing agents.

As the transition metal element, there may be mentioned, for instance, Group 3 elements of the Periodic Table of Elements (e.g., besides scandium Sc and yttrium Y, lanthanoid elements such as lanthanum La, cerium Ce, samarium Sm; actinoid elements such as actinium Ac), Group 4 elements of the Periodic Table of Elements (e.g., titanium Ti, zirconium Zr, hafnium Hf), Group 5 elements (e.g., vanadium V, niobium Nb, tantalum Ta), Group 6 elements (e.g., chromium Cr, molybdenum Mo, tungsten W), Group 7 elements (e.g., manganese Mn), Group 8 elements (e.g., iron Fe, ruthenium Ru, osmium Os), Group 9 elements (e.g., cobalt Co, rhodium Rh, iridium Ir), Group 10 elements (e.g., nickel Ni, palladium Pd, platinum Pt), and Group 11 elements (e.g., copper Cu, silver Ag, gold Au) of the Periodic Table of Elements.

Particularly, when combined with an imide compound of the formula (1), a compound containing a lanthanoid element such as Ce, a Group 4 element such as Ti, a Group 5 element such as V, a Group 6 element such as Mo and W, a group 7 element such as Mn, a Group 8 element such as Fe and Ru, a Group 9 element such as Co and Rh, a Group 10 element such as Ni, or a Group 11 element such as Cu exhibits high oxidation activity.

There is no specific restriction on the species of the co-oxidizing agent (co-catalyst or promoter) provided that it contains an element selected from the elements listed above and has the oxidizing ability. The co-oxidizing agent may be a hydroxide but is usually a metal oxide, an organic acid salt, an inorganic acid salt, a halide, a coordination compound (complex), a heteropolyacid, or a salt thereof containing an element of those listed above. Further, as the boron compound, there may be exemplified boron hydrides (e.g., borane, diborane, tetraborane, pentaborane, decaborane), boric acids (e.g., orthoboric acid, methaboric acid, tetraboric acid), borates (salts of boric acid) (e.g., nickel borate, magnesium borate, manganese borate), boron oxides such as $B_2O_3$, borazane, borazene, borazine, boron amide, boron imide, and other nitrogen-containing compounds, $BF_3$, $BCl_3$, tetrafluoroborate and other halides, and esters of boric acid (e.g., methyl borate, phenyl borate).

As the organic acid salt, there may be mentioned, for example, acetates, propionates, salts of naphthenic acid, and stearates, and examples of the inorganic acid are nitrates, sulfates, and phosphates. Moreover, as the halide, there may be exemplified chlorides and bromides.

As a ligand of the complex, there may be exemplified OH (hydroxo); alkoxy groups such as methoxy, ethoxy, propoxy and butoxy groups; acyl groups such as acetyl and propionyl groups; alkoxycarbonyl groups such as methoxycarbonyl (acetato) and ethoxycarbonyl groups; acetylacetonato, cyclopentadienyl group; halogen atoms such as chlorine and bromine; CO; CN; oxygen atom; $H_2O$ (aquo); phosphorus compounds such as phosphine (e.g., a triarylphosphine such as triphenylphosphine); and nitrogen-containing compounds such as $NH_3$ (ammine), NO, $NO_2$ (nitro), $NO_3$ (nitrato), ethylenediamine, diethylenetriamine, pyridine and phenanthroline. As to the complex or a complex salt, a single ligand or ligands of the same or different kinds may be coordinated therein.

Preferred complexes includes complexes containing a transition metal element selected from those mentioned above. The complex may be constituted of a combination of a transition metal element and a ligand that are suitably selected from teh above. For example, the preferred complex may be ceriumacetylacetonato, cobaltacetylacetonato, rutheniumacetylacetonato, or copperacetylacetonato.

A polyacid which forms the heteropolyacid contains, in many cases, at least one of the Group 5 elements or the Group 6 elements of the Periodic Table of Elements, such as V (vanadic acid), Mo (molybdic acid), and W (tungstic acid). There is no specific restriction as to the central atom. Concrete examples of the heteropolyacid are cobaltmolybdate, cobalttungstate, molybdenumtungstate, vanadiummolybdate, and vanadomolybdenumphosphate.

Incidentally, in the oxidizing catalyst, the heteropolyacid is thought to participate in a hydrogen abstraction reaction, and a cobalt-containing compound or a boron-containing compound are thought to participate in the decomposition of a peroxide.

An imide compound expressed by the formula (1) or a catalytic system comprised of the imide compound and the above-described co-oxidizing agent may be either homogeneous or heterogeneous. Further, the catalytic system may be a solid catalyst comprising a catalytic component supported on a support or carrier. The support is, in many instances, a porous support such as active carbon, zeolite, silica, silica-alumina, and bentonite. As to the amount of catalytic component supported on the support in the solid catalyst, the amount of the imide compound of the formula (1) is about 0.1 to 50 parts by weight relative to 100 parts by weight of the support. The amount of the co-oxidizing agent supported is, relative to 100 parts by weight of the support, about 0.1 to 30 parts by weight.

The amount of the imide compound of the formula (1) can be selected from within a wide range, and may for example be about 0.001 mol (0.1 mol %) to 1 mol (100 mol %), preferably about 0.01 mol (1 mol %) to 0.5 mol (50 mol %), more preferably about 0.05 (5 mol %)) to 0.30 mol (30 mol %), and usually about 0.05 mol (5 mol %) to 0.25 mol (25 mol %), relative to 1 mol of the substrate to be oxidized.

The amount of the co-catalyst (co-oxidizing agent) is, for example, about 0.001 mol (0.1 mol %) to 0.7 mol (70 mol %), preferably about 0.002 to 0.5 mol, more preferably about 0.002 to 0.3 mol, more preferably about 0.0023 to 0.1, particularly about 0.0023 to 0.2 mol, and usually 0.0025 to 0.1 mol, relative to 1 mol of the substrate to be oxidized.

The ratio of co-oxidizing agent to the imide compound of the formula (1) is: imide compound/co-oxidizing agent= 95/5 to 5/95 (molar ratio), preferably about 90/10 to 20/80 (molar ratio), and more preferably about 85/15 to 50/50 (molar ratio).

When the heteropolyacid or a salt thereof is used as the co-oxidizing agent, the amount thereof is, relative to 100 parts by weight of the substrate, about 0.1 to 25 parts by weight, preferably about 0.5 to 10 parts by weight, and more preferalby about 1 to 5 parts by weight.

When utilizing such oxidizing catalyst, even a hydrocabon which has long been thought to be very difficult to be oxidized can be oxidized with high efficiency. For example, in the prior art, an oxidation method whereby a hydrocarbon such as cyclohexane is converted through an oxidizing reaction at a conversion of 10% or higher has been regarded as an oxidation method of remarkable excellence, and good results are obtained only in a case with a peculiar substrate such as diphenylmethane. On the other hand, according to the present invention, an oxide of a carbonyl compound or an alcohol can be formed in a high yield (e.g., about 20 to 60%, or higher) by just stirring a catalytic amount of the aforementioned compound together with a corresponding saturated hydrocarbon as a substrate (e.g., cyclohexane) in an atmosphere of oxygen. Therefore, the process of the present invention is useful in introducing an oxygen-containing group into the substrate (e.g., hydroxyl group, carbonyl group, formyl group, carboxyl group).

In the oxidation process of the present invention, the substrate is oxidized by being brought into contact with molecular oxygen in the presence of the catalyst. As the substrate, there may be exemplified, besides hydrocarbons, alcohols, aldehydes, ketones, amines, and heterocyclic compouds, a variety of compounds such as thiols typified by ethanethiol and phenylmethanethiol; sulfides typified by diethyl sulfide, methyl propyl sulfide, and diphenyl sulfide; and amides typified by formamide and acetamide.

Preferred substrates include saturated or unsaturated hydrocarbons, alcohols, aldehydes, amines, and heterocyclic compounds. Hydroxy compounds, aldehyde compounds, ketones compounds, or organic acids are formed by oxidizing the corresponding hydrocarbons. Moreover, aldehydes (formyl) compounds, ketones, or organic acids are formed by oxidizing corresponding alcohols, and organic acids are produced by oxidizing corresponding aldehyde compounds. Furthermore, ketones are cleaved by oxidation, forming corresponding aldehyde (formyl) compounds, or organic acids.

Hydrocarbons include saturated or unsaturated hydrocarbons, e.g., straight- or branched chain aliphatic hydrocarbons inclusive of higher hydrocarbons (e.g., branched chain-type saturated hydrocarbons such as isobutane; branched chain-type unsaturated hydrocarbons such as 2-butene, isobutene, butadiene and isoprene); alicyclic hydrocarbons exemplified by $C_{3-20}$ cycloalkanes typified by cyclobutane, cyclopentane, cyclohexane, cycloheptane, cyclooxtane, methylcyclohexane, ethylcyclohexane, dimethylcyclohexane, chlorocyclohexane, methoxycyclohexane, and cyclooctane, cycloalkenes typified by cyclohexene and cyclooctene, and cycloalkadienes typified by cyclopentadiene and cyclooctadiene, and bridged cyclic hydrocarbons (including dicyclopentadiene, adamantane, terpenes such as limonene, terpinene, and α-pinene); condensed ring-type hydrocarbons such as completely or partially hydrogenated condensed polycyclic hydrocarbons (acenaphthene, indene, fluorene, tetralin); aromatic hydrocarbons such as diphenylmethane, triphenylmethane, dibenzyl, and stilbene; and aromatic hydrocarbons having at least one alkyl group such as toluene, xylene, and ethylbenzene.

Preferred hydrocarbons include (i) compounds having a carbon-hydrogen bond at a site adjacent to an unsaturated bond (e.g., compounds having a carbon-hydrogen bond at an allyl site or a benzyl site); (ii) non-aromatic cyclic hydrocarbons (e.g., cycloalkanes such as cyclohexane and methylcyclohexane; cycloalkenes such as cyclohexene); (iii) condensed ring-type compounds including non-aromatic rings (e.g., cycloalkane rings, heterocycles); and (iv) bridged cyclic hydrocarbons including a tertiary carbon (methine carbon).

As alcohols, there may be exemplified saturated aliphatic monohydric alcohols such as methanol, ethanol, 1-propanol, isopropanol, 1-butanol, isobutanol, 1-pentanol, 2-pentanol, neopentanol, 1-hexanol, 1-octanol, 1-decanol, and higher alcohols (e.g., 1-dodecanol, myristyl alcohol, 1-hexadecanol); unsaturated aliphatic monohydric alcohols such as allyl alcohols, crotyl alcohol, propargyl alcohol, geraniol, and citronellol; aliphatic polyhydric alcohols such as ethylene glycol, propylene glycol, trimethylene glycol, 1,2-butanediol, 1,3-butanediol, 1,4-butanediol, hexanediol, neopentyl glycol, pinacol, and glycerol; alicyclic monohydric alcohols such as cyclobutanol, cyclopentanol, cyclohexanol, methylhexanol, cyclohexen-1-ol, 4-hydroxy-1-cyclohexane carboxylic acid, cycloheptanol, cyclooctanol, borneol, and menthol; alicyclic polyhydric alcohols such as 1,2-cyclohexanediol and 1,4-cyclohexanediol; and aromatic alcohols such as benzyl alcohol, salicyl alcohol, benzhydrol, and phenethyl alcohol.

Of these alcohols, primary or secondary alcohols are preferable, and they may be aliphatic alcohols, alicyclic alcohols, or aromatic alcohols. Incidentally, the oxidation process of the present invention is characterized in that an oxidizing reaction proceeds with preference to primary alcohols.

Preferred alcohols include (v) compounds having a hydroxymethyl group at a site adjacent to an unsaturated bond (e.g., unsaturated alcohols or aromatic alcohols such as allyl alcohol, benzyl alcohol, and benzhydrol); (vi) alicyclic alcohols (e.g., cycloalkanols such as cyclohexanol and methylhexanol); (vii) alicyclic alcohols having tertiary carbon (methine carbon) (e.g., borneol).

As aldehydes, there may be mentioned aliphatic aldehydes such as saturated aliphatic aldehydes [e.g., formaldehyde, acetaldehyde, propionealdehyde, butylaldehyde, hexanal, higher aldehydes (e.g., octaldehyde, nonaldehyde)], unsaturated aliphatic aldehydes (e.g., acrolein), glyoxal, methylglyoxal, aliphatic polyaldehydes (e.g., malonaldehyde, succinaldehyde, glutaraldehyde, adipinaldehyde, pimelic aldehyde, suberic aldehyde, sebacic aldehyde), and aminoacetaldehyde; aromatic aldehydes such as benzaldehyde, oxybenzaldehyde, nitrobenzaldehyde, aminobenzaldehyde, cinnamaldehyde, salicylaldehyde, anisaldehyde, 1-naphthylacetaldehyde, vanillin (vanillaldehyde), phthalaldehyde, isophthalaldehyde, and terephthalaldehyde; alicyclic aldehydes such as formylcyclohexane, citronellal, and citral; and heterocyclic aldehydes such as nicotinaldehyde and furfural.

As ketones, there may be exemplified aliphatic ketones such as acetone, methyl ethyl ketone, diethyl ketone, dipropyl ketone, methyl propyl ketone, methyl butyl ketone, and pinacolone; alicyclic ketones (cyclic ketones) such as cyclopentanone, cyclohexanone, cyclooctanone, 2-methyl cyclohexanone, 2-ethylcyclohexanone, 2,6-dimethylcyclohexanone, 4-chlorocyclohexanone, 4-methoxycyclohexanone, menthone, and camphor; aromatic ketones such as acetophenone, propiophenone, benzophenone, deoxybenzoin, and 1-naphthalenone; and heterocyclic ketones such as inden-1-one, 1,2,3-indantrione, fluoren-9-one, and 4-pyranone.

As amines, there may be mentioned, for example, primary or secondary amines such as aliphatic amines typified by methyamine, ethylamine, propylamine, butylamine, dimethylamine, diethylamine, dibutylamine, ethylenediamine, 1,4-butanediamine, hydroxylamine, and ethanolamine; alicylic amines typified by cyclopentylamine and cyclohexylamine; and aromatic amines typified by benzylamine and toluidine. Amines are oxidized into the corresponding Schiff bases or oximes by oxidation.

As heterocyclic compounds, there may be exemplified non-aromatic heterocyclic compounds and condensed ring-type hydrocarbons containing a non-aromatic heterocycle, such as pyran, pyrazoline, piperidine, piperazine, indoline, isoindoline, chromene, xanthene, chroman, and isochroman. Heterocyclic compounds include aromatic heterocyclic compounds having at least one alkyl group, such as methylpyridine.

The molecular oxygen to be used for the oxidation of the substrate is not particularly restricted, and oxygen diluted with an inert gas such as nitrogen, helium, argon, or carbon dioxide may be employed as well as pure oxygen. From the view points of not only operability and safety but also economy, air is preferably used.

The quantity of molecular oxygen is usually, relative to 1 mol of the substrate compound, 0.5 mol or more (e.g., 1 mol or more), preferably about 1 to 100 mol, and more preferably about 2 to 50 mol. In many instances, an excess mol of molecular oxygen is used relative to the amount of the substrate.

The oxidation process of the present invention is usually carried out in an organic solvent insusceptible to the reaction. Examples of the organic solvent are organic acids such as acetic acid and propionic acid; nitriles such as acetonitrile, propionitrile, and benzonitrile; amides such as formamide, acetamide, dimethylformamide (DMF), and dimethylacetamide; alcohols such as t-butanol and t-amyl alcohol; aromatic hydrocarbons such as benzene; halogenated hydrocarbons such as chloroform, dichloromethane, dichloroethane, carbon tetrachloride, and chlorobenzene; nitro compounds such as nitrobenzne, nitromethane, and nitroethane; esters such as ethyl acetate and butyl acetate; ethers such as dimethyl ether, diethyl ether, diisopropyl ether, dioxane, and tetrahydrofuran; and mixed solvents thereof. Incidentally, the substrate may serve as a reaction solvent by using excessively. As the solvent, in many cases, a nitrile or an amide is employed.

The present invention is characterized in that an oxidation reaction is carried out in a reaction system with a low water content. When an oxidation reaction is carried out in such reaction system, the generation of by-products is inhibited, and the oxidation can smoothly be effected without deteriorating the high activity of the oxidizing catalyst or the co-oxidizing agent. The water content of the oxidizing reaction system is, relative to 1 mol of the imide compound represented by the formula (1), 200 mol or lower (e.g., about 0 to 150 mol), preferably 100 mol or lower (e.g., about 0 to 70 mol), more preferably 50 mol or lower (e.g., about 0 to 30 mol), and particularly 25 mol or lower (e.g., about 0 to 10 mol, especially about 0 to 5 mol).

The water content need only be adjusted at least at the beginning of the oxidizing reaction. In the reaction system, the starting material(s), the solvent(s), and the catalyst(s) cannot always be kept away from moisture, but the water content may be adjusted by selecting suitable components constituting the reaction system or through a conventional operation.

Moreover, a water content of the oxidizing reaction system may be maintained within the above range by removing water produced by the oxidizing reaction from the reaction system in conventional manner (e.g. distillation). When an oxidizing reaction is conducted in an organic solvent, water resulted from the oxidizing reaction, the solvent and the compound having an imide unit of the formula (1) are separated from the reaction products, and the solvent separated is recyclable to the reaction system.

The process of the present invention is characterized in that an oxidizing reaction smoothly proceeds even under relatively mild conditions. The reaction temperature can suitably be selected according to the species of the substrate, and is for example about 0 to 300° C., preferably about 30 to 250° C., and more preferably about 50 to 200° C. Usually, the reaction is effected at a temperature of about 70 to 150° C. Moreover, the reaction may be effected under atmospheric pressure or under applied pressure. When conducting the reaction under applied pressure, the pressure is usually about 1 to 100 atm (e.g., 1.5 to 80 atm), preferably about 2 to 70 atm, and more preferably about 5 to 50 atm. The reaction time can be selected from within the range of, e.g., about 1 minute to 48 hours, preferably about 1 to 36 hours, and more preferably about 2 to 24 hours, and the choice depends on the reaction temperature and pressure.

Incidentally, it is possible to raise the rate of oxidation reaction by effecting the reaction at a higher reaction temperature and/or under higher reaction pressure, but a carboxylic acid or a peroxide may sometimes be by-produced.

The process of the present invention is useful in producing alcohols, aldehydes, ketones, and organic acids by, as described above, oxidizing a variety of compounds under mild conditions at high conversions and selectivities. Particularly, the use of cycloalkane which may have a substituent as the substrate makes it possible to provide, under mild conditions, cycloalkanol, a cycloalkanone, and a dicarboxylic acid which may have the corresponding substituent in high yields while inhibiting side reactions. Therefore, cylohexanol, cyclohexanone, and adipic acid are formed by employing cyclohexane as the substrate. Moreover, cyclohexanol and cyclohexanone (KA oil) can be converted finally to adipic acid by oxidation. Accordingly, the oxidation process of the present invention is very useful when producing adipic acid as a starting material of nylon 66 by bringing at least one component of cyclohexane, cyclohexanol, and cyclohexanone into contact with molecular oxygen, as well as being very useful as a process for producing alcohols, aldehydes, ketones, and organic acids.

In the presence of or in a stream of molecular oxygen, the reaction can be carried out in a conventional manner, such as in a batch system, a semi-batch system, or a continuous system. After completion of the reaction, the reaction product can be easily separated and purified though a conventional operation, such as separation means typified by filtration, condensation, distillation, extraction, crystallization, recrystallization, or column chromatography, or a combination means thereof. In the solvent-recovering step or separation-purification step, the reaction system can be dehydrated according to a process which is generally industrially employed.

INDUSTRIAL APPLICABILITY

According to the present invention, since the oxidation reaction system comprises a specific catalyst and the substrate is oxidized with the oxidation reaction system of a low water content, it is possible to provide the object compound with high purity and in a high yield while inhibiting the generation of a by-product(s) and deactivation of an oxidizing catalyst or an oxidation catalytic system. Furthermore, even under mild conditions, the substrate is smoothly oxidizable using molecular oxygen. Therefore, the present invention is useful in producing alcohols, carbonyl compounds, aldehyde compounds, and organic carboxylic acids (particularly, KA oil and adipic acid) with high purity and in high yields under mild conditions.

Hereinafter, the present invention will be described in further detail based on the examples and should by no means be construed as defining the scope of the invention.

EXAMPLES

Example 1

A mixed solution [N-hydroxyphthalimide:water=1:2.8 (molar ratio)] comprised of cyclohexane [840 g (10 mol); water content 0.042 g (2.3 mmol)], N-hydroxyphthalimide [160 g (0.98 mol); water content 5 g (0.28 mol)], and acetonitrile [10,000 g; water content 45 g (2.5 mol)] was stirred at 75° C. and under an oxygen pressure of 20 atm for 10 hours. The product in the reaction mixture was examined by gas chromatography and there was observed the presence of cyclohexanone converted from cyclohexane at a conversion of 56% and a selectivity of 60%. After the solvent acetonitrile and the catalyst N-hydroxyphthalimide have been separated from the reaction crude mixture, the resultant solution was treated such as to be neutral. After undergoing the recovering step of the starting material cyclohexane, from the solution was obtained the product cyclohexanone. The purity of the obtained product cyclohexanone was 99% and the purification yield was 92%.

Comparative Example 1

Cyclohexanone was produced in the same manner as in Example 1 except that the water content of cyclohexanone was 0.050 g (2.8 mmol), the water content of N-hydroxyphthalimide was 8 g (0.44 mol), and that the water content of acetonitrile was 3,700 g (205 mol) [N-hydroxyphthalimide:water=1:210 (molar ratio)]. The purity of the obtained product cyclohexanone was 91%, and the purification yield was 80%.

Example 2

A mixed solution [N-hydroxyphthalimide:water=1:3.5 (molar ratio)] of cyclohexane [840 g (10 mol); water content 0.032 g (1.7 mmol)], N-hydroxyphthalimide [160 g (0.98 mol); water content 3 g (0.17 mol)], cobaltacetylacetonato [64 g (0.025 mol)], and acetonirile [10,000 g; water content 60 g (3.3 mol)] was stirred at 75° C. and under an oxygen pressure of 20 atm for 10 hours. The product formed in the reaction solution was examined by gas chromatography and there was observed the presence of cyclohexanone converted from cyclohexane at a conversion of 56% and a selectivity of 67%. After the solvent acetonitrile and the catalyst N-hydroxyphthalimide have been separated from the crude reaction solution, the resultant mixture was treated such as to be neutral. Thereafter, the solution went through the recovering step of the starting material cyclohexane, and there was obtained the product cyclohexanone. The purity of the obtained product cyclohexanone was 99%, and the purification yield was 93%.

Comparative Example 2

Cyclohexanone was formed in the same manner as in Example 2 except that the water content of cyclohexane was 0.048 g (2.7 mmol), the water content of N-hydroxyphthalimide was 9 g (0.5 mol), and that the water content of acetonitrile was 3,850 g (214 mol) [N-hydroxyphthalimide:water=1:219 (molar ratio)]. The purity of the product cycloexanone was 92% and the purification yield was 81%.

What is claimed is:

1. An oxidation process which comprises an oxidation reaction effected by bringing a substrate into contact with molecular oxygen in the presence of a compound having an imide unit represented by the following formula (1):

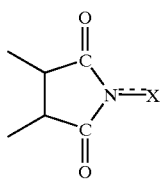

(1)

in which X stands for an oxygen atom or a hydroxyl group, wherein the oxidation reaction is carried out in a continuous reaction system which results in water from the oxidation reaction, while maintaining the water content of the reaction system at 200 mol or lower relative to 1 mol of the compound having the imide unit by removing water produced by the oxidizing reaction from the oxidizing reaction system.

2. An oxidation process according to claim 1, wherein the compound having an imide unit is expressed by the following formula (2):

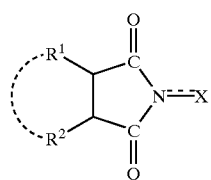

(2)

wherein $R^1$ and $R^2$ are the same or different, each representing a hydrogen atom, a halogen atom, an alkyl group, an aryl group, a cycloalkyl group, a hydroxyl group, an alkoxy group, a carboxyl group, an alkoxycarbonyl group, or an acyl group; $R^1$ and $R^2$ may be coupled together to form a double bond, or an aromatic or non-aromatic ring; the aromatic or non-aromatic ring composed of $R^1$ and $R^2$ may have at least one imide unit of the formula (1); and X has the same meaning as defined above.

3. An oxidation process according to claim 2, wherein $R^1$ and $R^2$ is coupled together to form a cyclohexane ring which may have a substituent, a cyclohexene ring which may have a substituent, a 5-norbornene ring which may have a substituent, or a benzene ring which may have a substituent.

4. An oxidation process according to claim 1, wherein the compound having an imide unit represented by the formula (1) is used in combination with a co-oxidizing agent to form an oxidizing catalyst.

5. An oxidation process according to claim 4, wherein the co-oxidizing agent is a compound containing at least one element selected from the group consisting of a Group 3 element, a Group 4 element, a Group 5 element, a Group 6 element, a Group 7 element, a Group 8 element, a Group 9 element, a Group 10 element, a Group 11 element, and a Group 13 element.

6. An oxidation process according to claim 1, wherein the substrate is at least one member selected from (i) a hydrocarbon compound having a carbon-hydrogen bond at an allyl site or a benzyl site, (ii) a cycloalkane which may have a substituent, (iii) a condensed ring-type hydrocarbon containing a cycloalkane ring or a non-aromatic heterocycle, (iv) a bridged cyclic hydrocarbon containing a tertiary carbon, (v) a compound having a hydroxylmethyl group at a site adjacent to an unsaturated bond, (vi) an alicyclic alcohol, (vii) an alicyclic alcohol having a tertiary carbon, (viii) an aldehyde compouond, and (ix) a ketone.

7. An oxidation process according to claim 1, wherein the cycloalkane which may have a substituent is oxidized with molecular oxygen to form the corresponding cycloalkanone, cycloalkanol, or dicarboxylic acid.

8. An oxidation process according to claim 1, wherein the water content of the oxidizing reaction system is 0 to 50 mol relative to 1 mol of the compound having an imide unit of the formula (1).

9. An oxidation process according to claim 1, wherein 0.01 to 0.5 mol of the compound having an imide unit of the formula (1) relative to 1 mol of a substrate is used, and the water content of the oxidizing reaction system may be maintained of about 0 to 30 mol relative to 1 mol of the compound having an imide unit of the formula (1).

10. An oxidation process according to claim 9, wherein the compound having an imide unit represented by the formula (1) is used in combination with 0.001 to 0.1 mol of a co-oxidizing agent relative to 1 mol of a substrate to form an oxidizing catalyst.

11. An oxidation process according to claim 1, wherein the water content of the oxidizing reaction system is maintained within the range of 0 to 30 mol relative to 1 mol of the compound having an imide unit of the formula (1) by the removal of water produced by the oxidizing reaction from the oxidizing reaction system.

12. An oxidation process according to claim 1, wherein the oxidizing reaction is conducted in an organic solvent, water resulted from the oxidizing reaction, the solvent and the compound having an imide unit of the formula (1) are separated from reaction products and the solvent separated is recyclable to the oxidizing reaction system.

* * * * *